United States Patent [19]
Barrelle et al.

[11] Patent Number: 6,027,481
[45] Date of Patent: Feb. 22, 2000

[54] PREFILLABLE SYRINGE

[75] Inventors: Laurent Barrelle, Grenoble; Francois Mansour, Seyssins, both of France

[73] Assignee: Becton Dickinson and Company, Franklin Lakes, N.J.

[21] Appl. No.: 09/264,125

[22] Filed: Mar. 8, 1999

[51] Int. Cl.[7] ............................................. A61M 5/00
[52] U.S. Cl. ..................... 604/187; 604/90; 604/191; 604/232
[58] Field of Search ....................... 604/218, 187, 604/82, 90, 89, 191, 232

[56] References Cited

U.S. PATENT DOCUMENTS

| | | |
|---|---|---|
| 3,967,759 | 7/1976 | Baldwin et al. . |
| 3,995,630 | 12/1976 | Van der Veerdonk . |
| 4,031,890 | 6/1977 | Homan . |
| 4,235,235 | 11/1980 | Bekkering . |
| 4,466,426 | 8/1984 | Blackman ............... 604/187 |
| 4,496,344 | 1/1985 | Kamstra .................. 604/90 |
| 4,599,082 | 7/1986 | Grimard . |
| 4,613,326 | 9/1986 | Szwarc . |
| 4,792,329 | 12/1988 | Schreuder ............ 604/191 X |
| 4,929,230 | 5/1990 | Pfleger . |
| 4,964,866 | 10/1990 | Szwarc . |
| 4,986,818 | 1/1991 | Imbert et al. . |
| 5,282,792 | 2/1994 | Imbert ...................... 604/187 |
| 5,599,312 | 2/1997 | Higashikawa ........... 604/218 X |
| 5,607,400 | 3/1997 | Thibault et al. . |
| 5,836,919 | 11/1998 | Skurka et al. . |

FOREIGN PATENT DOCUMENTS

| | | |
|---|---|---|
| 0 340 880 A2 | 11/1989 | European Pat. Off. . |
| 0 720 857 A1 | 7/1996 | European Pat. Off. . |
| 0 723 784 A1 | 7/1996 | European Pat. Off. . |

OTHER PUBLICATIONS

Review of Glass Types Available for Packaging Parenteral Solutions, S.V. Sangra Journal of the Parenteral Drug Association, Mar.–Apr., 1979, vol. 33 No. 2, pp. 61–67.

*Primary Examiner*—John D. Yasko
*Attorney, Agent, or Firm*—Allen W. Wark

[57] ABSTRACT

A prefillable syringe includes an elongate barrel having an open distal end and a proximal end with at least one chamber formed therebetween for receiving a substance sensitive to pH shift, such as water for injection. The barrel is made of a low extractable ion glass preferably having a low concentration of sodium of less than 8% and preferably around 4% or less.

11 Claims, 5 Drawing Sheets

FIG-2
FIG-3
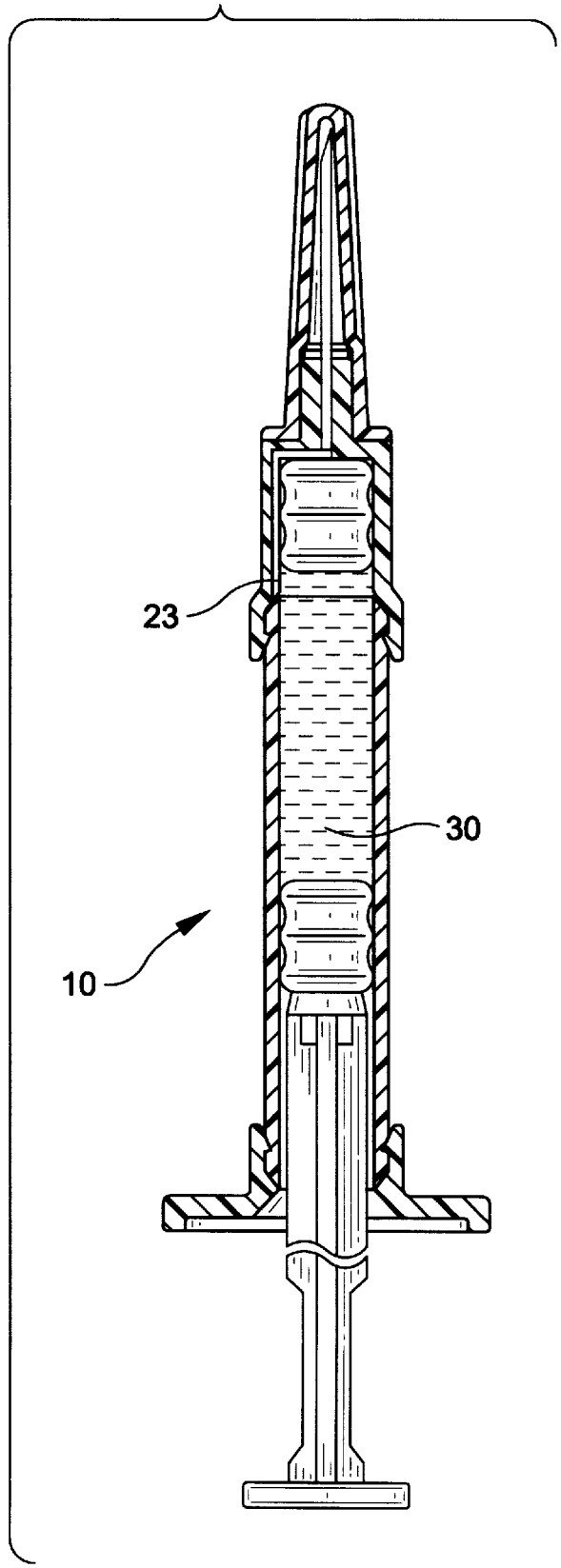
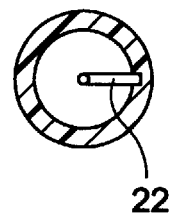

PREFILLABLE SYRINGE

FIELD OF THE INVENTION

The present invention generally relates to syringes, and more specifically relates to a prefillable syringe made of a low extractable ion glass, which is particularly suited for being prefilled with substances sensitive to pH shift such as for example water for injection.

BACKGROUND OF THE INVENTION

Prefillable glass syringes are well known to those skilled in the art and typically include an elongate barrel having opposed proximal and distal ends and at least one chamber therebetween for receiving a substance such as a fluid. Basically there are two types of syringes, i.e., one type in which one end of the barrel is formed to include a tip portion and the other end is formed to include a flange portion and a second type in which both ends of the barrel remain basically unformed in comparison to the first type. Examples of the first type of such syringes having a single chamber are disclosed in U.S. Pat. Nos. 4,964,866 (Szwarc), 4,986,818 (Imbert et al.) and 5,607,400 (Thibault et al.) and having multi-chambers are disclosed in U.S. Pat. Nos. 4,599,082 (Grimard), 4,613,326 (Szwarc) and 4,929,230 (Pfleger), and examples of the second type are disclosed in U.S. Pat. No. 4,235,235 (Bekkering) and EPO Patent No. 340,880 (Schreuder), the disclosures of which are hereby incorporated by reference in their entirety.

However, several disadvantages and limitations have been associated with the use of such syringes when prefilled with substances sensitive to pH shift and stored over an extended period of time, including shifts in pH outside the acceptable Pharmacopiea range of 5–7 for water for injection. Attempts to reduce or minimize such unacceptable shifts in the level of pH have included treating the glass by methods such as those disclosed in an article by S. V. Sanga entitled "Review of Glass Types Available for Packaging Parenteral Solutions," Journal of Parenteral Drug Association, Vol. 33, No. 2, pgs. 61–67 (March-April 1979). Nevertheless, despite such attempts pH shifts remain.

Thus, there has been a need for a prefillable syringe which would eliminate or at least minimize the problems and limitations associated with the prior syringes discussed above, most significant of the problems being unacceptable shifts in the pH level of the substance filled in the syringe.

SUMMARY OF THE INVENTION

In contrast to the prior syringes discussed above, it has been found that a prefillable syringe particularly suited for being prefilled with pH sensitive substances, such as water for injection, can be constructed in accordance with the present invention. Specifically, the syringe is made of a low extractable ion glass having a sodium content less than 8%, and preferably around 4% or less.

The prefillable syringe of the present invention includes an elongate barrel having a proximal end and a distal end, with at least one chamber formed between the ends. A plunger is sealably disposed within the barrel and movable with respect thereto, and sealing means is sealably disposed approximate the distal end of the barrel, with at least one substance sensitive to pH shift situated in the chamber. The barrel is made of a low extractable ion glass whereby over an extended period of time, the pH of the substance disposed in the chamber of the barrel is maintained within a desirable range.

In the preferred embodiment of the prefillable syringe, the substance is water for injection which has a pH in the range of 5 to 7. In addition, the range of pH can be maintained over a period of time of at least 24 months.

In the preferred embodiment, the prefillable syringe of the present invention includes a generally cylindrical barrel in the shape of a hollow cylinder made of a low extractable ion glass with an open front end, a plunger, sealably disposed within the barrel and movable with respect thereto, a cylindrical stopper, having an outside diameter which is slightly larger than an inside diameter of the barrel and including means which seal the front end of the barrel, and a needle holder, including a collar which is attached in sealing relationship to the front end of the barrel, a neck for sealable attachment to an injection needle, the neck having a rotationally symmetric rear face which includes an aperture which functions to conduct fluid to the needle, and a hollow, internally cylindrical shaft having a rear end which is sealably connected to the collar and a front end which is sealably connected to the neck, wherein the inner walls of the shaft and the rear face of the neck define one or more slots which extend from the rear end of the shaft to the aperture.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 2 shows the syringe of FIG. 1 in a condition in which it is ready for administering an injection.

FIG. 3 is a cross-sectional view through the needle holder of the syringe shown in the preceding Figures, taken on the line III—III of FIG. 1, viewed in the direction of the needle.

DETAILED DESCRIPTION OF THE PREFERRED EMBODIMENT

Figure 1:
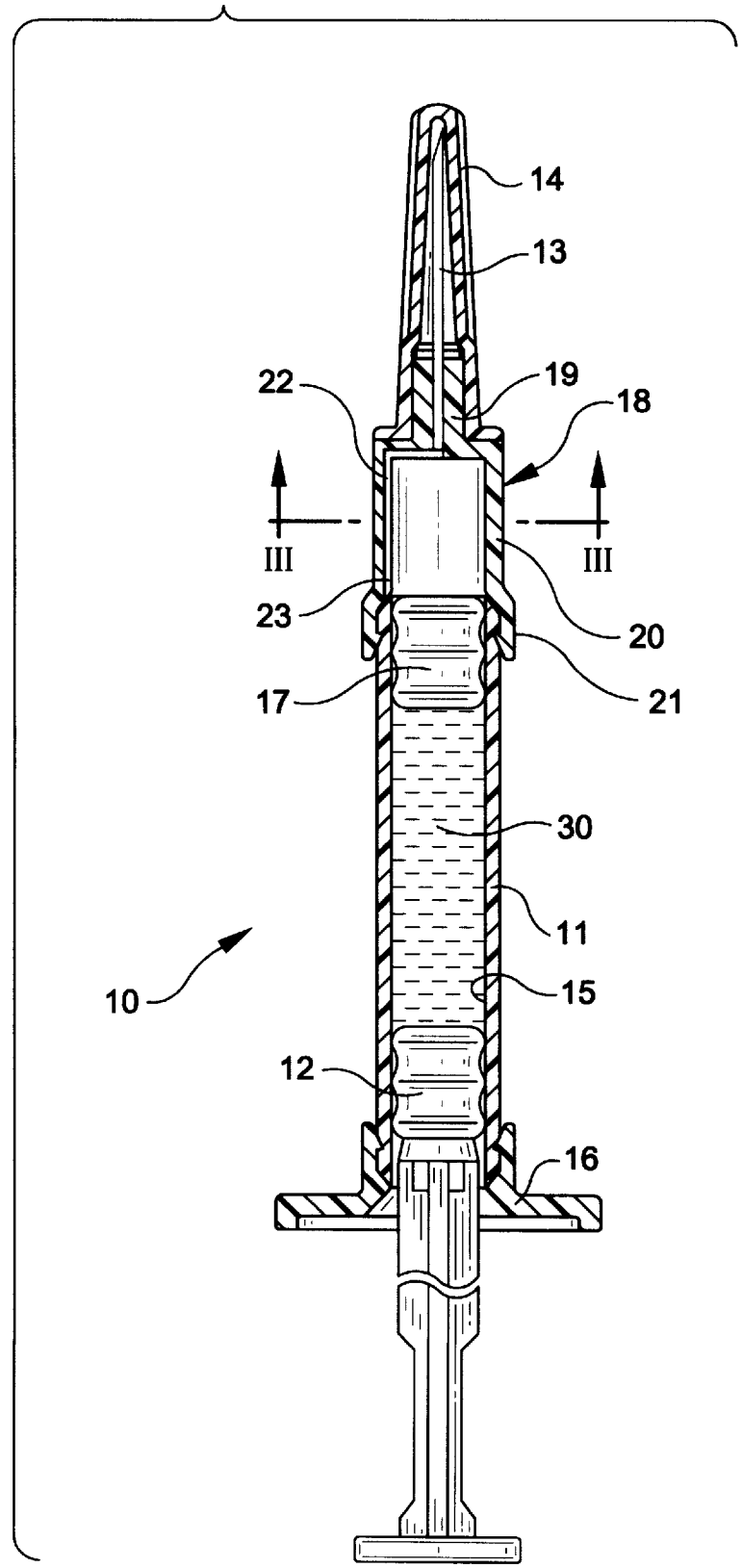
FIG. 1 is a longitudinal sectional view of a syringe in a condition in which it can be transported and stored.

The prefillable syringe of the present invention is illustrated in FIGS. 1–6, and generally includes the designation 10. Referring to FIG. 1, the syringe 10 of the present invention includes an elongate barrel or cylinder 11, in which a plunger 12 is provided on one end (the open proximal end) while the other end includes a needle-guard 14 (the distal end), with at least one hollow chamber 15 formed between the proximal and distal ends for receiving a substance. The needle-guard 14 keeps the syringe as well as the needle sterile during storage.

The plunger can be moved by means of a plunger rod, which is secured to the plunger, for example, by screwing. At the same end where the plunger is situated, the barrel has a fingergrip 16, which is secured to the barrel according to the so-called snap-cap principle. The fingergrip preferably consists of slightly resilient material, for example plastics. The barrel is manufactured from a low extractable ion glass material, the details of which are discussed hereinbelow. In another embodiment the fingergrip is a flangelike part of the barrel projecting radially outwards. Of course, other constructions known to those skilled in the art are possible.

A stopper 17, which closes the barrel, is situated in the end of the barrel remote from the plunger. The plunger and the stopper are manufactured from an elastic material, preferably rubber of a pharmaceutical quality.

The injection needle 13 is secured to the barrel by means of a needle holder 18. The needle holder has a neck 19, which holds the needle, a shaft 20 and a collar 21. The needle holder is preferably manufactured from slightly resilient material, which, however, has resistance to deformation for example, plastics and is secured to the end of the barrel by means of a snap-cap construction. In another embodiment the needle holder may be secured to the barrel by means of a screwed or adhesive connection or, when the barrel also comprises a collar, by means of a clamping ring; in the latter embodiment the needle holder may also be flanged around a collar of the barrel.

One or more slots 22 are recessed in the inner wall of the shaft 20 and the rear face of the neck. This is shown in detail in FIG. 3 which is a cross-sectional view through the shaft of the needle holder taken on the line III—III of FIG. 1 and viewed in the direction of the needle. One slot is shown in FIG. 3 however more slots may be provided in the needle holder. The slot or slots extend into the rear end of the cannula. In cross-section the slots may be parts of a circle, as shown in FIG. 3, but other shapes are also possible, provided the size is such that sufficient injection liquid can be readily passed through; this is achieved if the diameter of the slot or the overall cross-section of the slots is at least as large as that of the cannula. The shaft of the needle holder is constructed so that when the stopper slides axially forward, it is received, with friction, by the shaft; therefore, apart from the slots recessed in the shaft, the inside diameter of the shaft is approximately as large as that of the barrel 11. The shaft of the needle holder is slightly longer than the stopper so that the part 23 of the slot(s) adjoining the barrel is free when the stopper is moved forward against the rear wall of the neck of the needle holder. This is shown clearly in FIG. 2 in which the syringe of FIG. 1 has been activated, that is, moved in the position in which it is ready for administering an injection. In this position the injection liquid can reach the cannula without hindrance via the slots. If desired, the needle protector may be constructed to also serve as a plunger rod. In that case, prior to the administration of an injection, the needle protector is removed from the needle and secured at the other end of the syringe to the plunger.

Generally, a syringe comprising a needle protector has a safety member, which indicates whether the needle protector has previously been removed. Such a safety member in the form of a cap is described, for example, U.S. Pat. No. 3,995,630.

Figure 4:
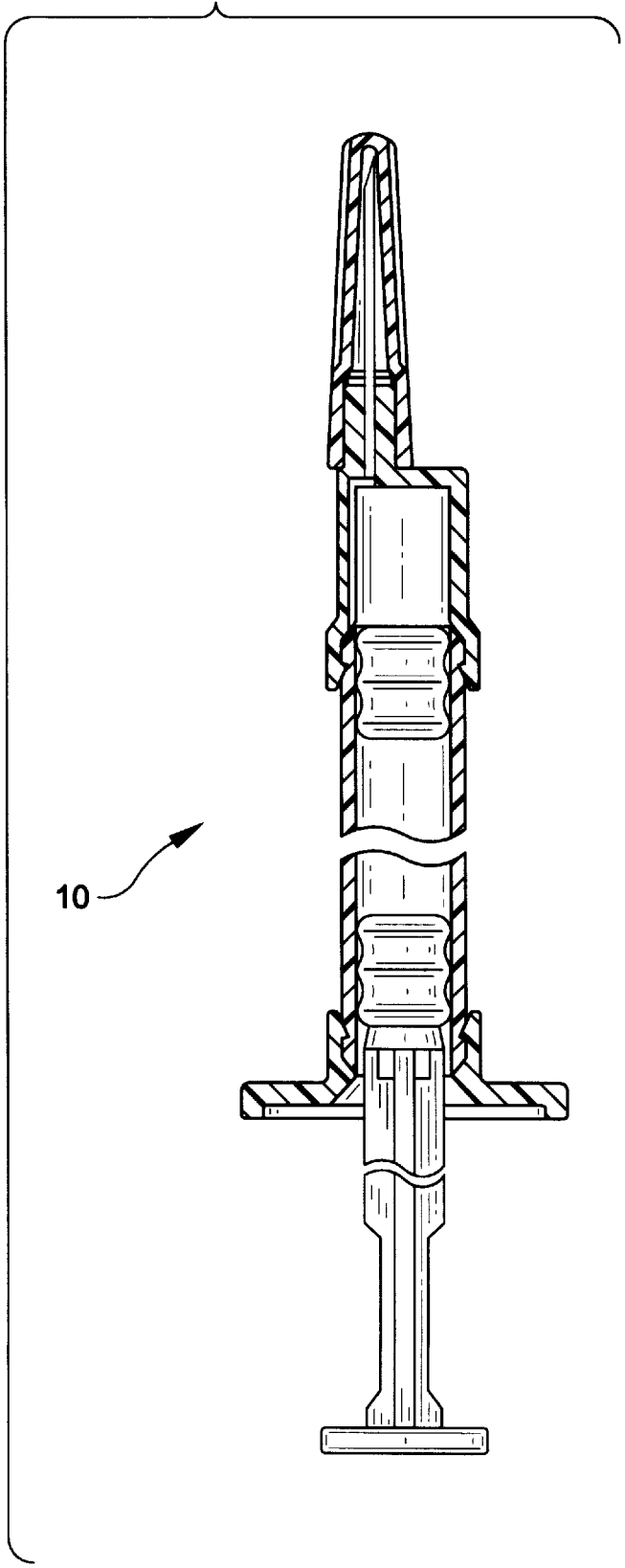
FIGS. 4, 5 and 6 are longitudinal sectional views of other embodiments of the invention.

In another embodiment, a longitudinal cross sectional view of which is shown in FIG. 4, the needle is eccentric to the barrel. Such a construction is sometimes desired in syringes having a large barrel diameter.

Figure 5:
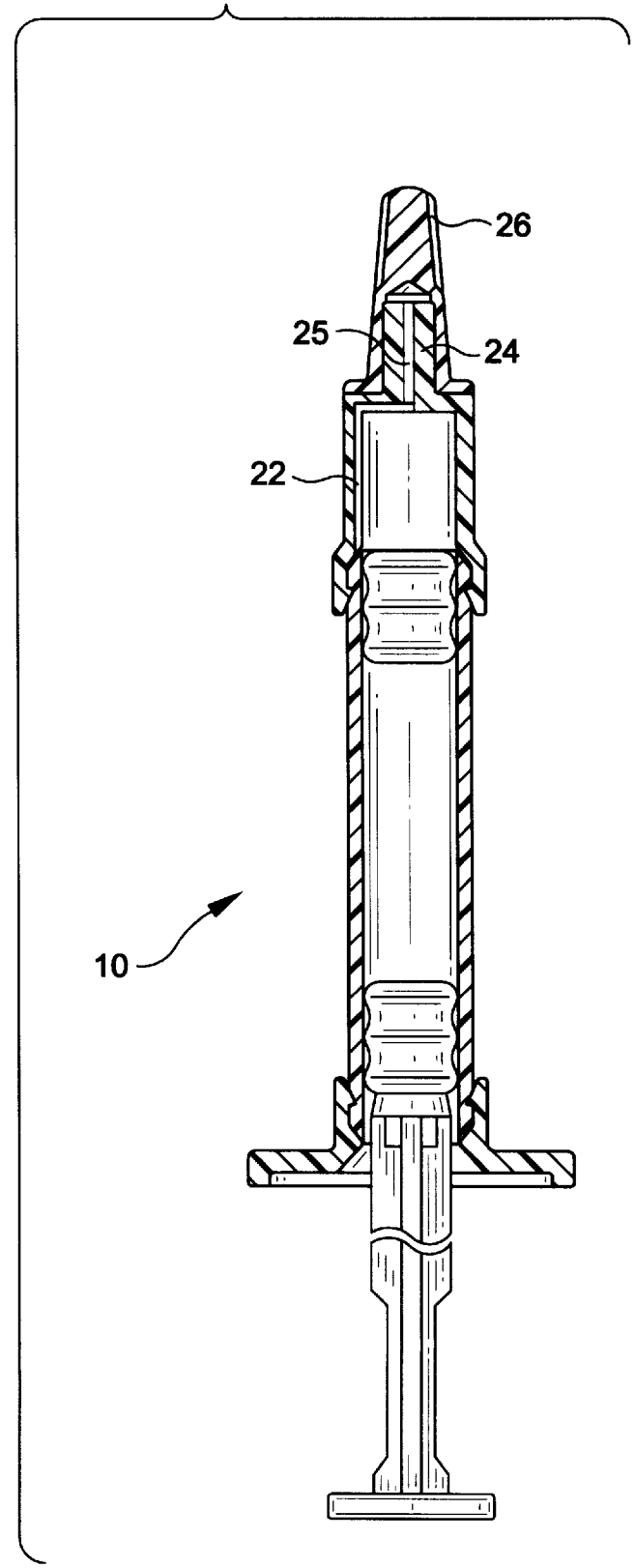

In another embodiment, a longitudinal sectional view of which is shown in FIG. 5, the syringe is not stored with a needle in position. Before use, the needle is positioned on the neck 24 of the needle holder by means of a needle hub. A so-called Luer cone is preferably used for this connection. In this embodiment aperture 25 in the neck of the needle holder is closed on the outside by a protective cap 26, which ensures the sterility of the syringe as well as the needle holder. Slot 22 recessed in the needle holder projects into the end of the neck aperture.

Figure 6:
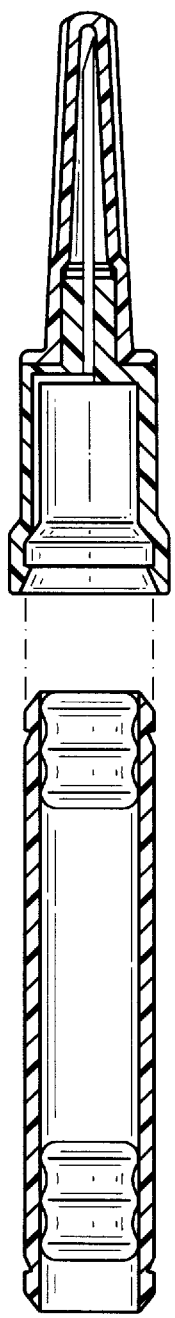

FIG. 6 shows a two-part embodiment of the syringe. The needle holder with injection needle may also be constructed as a needle holder with a Luer cone; in that case the needle is supplied separately. The connection of needle holder to barrel is shown as a snap-cap construction. In a likewise efficacious construction each end of the barrel comprises a flange projecting radially outwards and forming one assembly with the barrel; on the rear side the flange forms a finger grip, on the front side it forms a connection for the needle holder. In order to facilitate dispensing, the barrel is preferably symmetrical on two sides.

The end face of the stopper directed rearwardly and the end face of the plunger directed forwardly are both preferably rotationally symmetrical and complementary in order to minimize the residual volume of medicine. In a further preferred embodiment of the syringe, both faces are substantially flat. In addition, the front face of the stopper and the rear face of the neck of the needle holder, apart from the slot or slots recessed in said rear face, are preferably complementary surfaces; in this preferred embodiment of the syringe the quantity of medicine remaining in the syringe after the injection also is as small as possible.

The syringe embodying the present invention may also comprise a so-called "final filter" which serves to stop undesirable material such as "particulate matter", if any, present in the injection liquid. Such a filter is preferably placed on the rear side in the duct in the neck of the needle holder, for example, in a cavity recessed for this purpose between the needle and the rear face of the neck.

Experiments were conducted using the following composition of the glass in connection with the embodiment of the syringe 10 of the present invention illustrated in FIGS. 1–6:

EXAMPLE 1

| Oxide | % in Glass Composition |
|---|---|
| $SiO_2$ | 81 |
| $B_2O_3$ | 13 |
| $Al_2O_3$ | 2 |
| $Na_2O + K_2O$ | 4 |
| $CaO + MgO$ | <0.1 |
| BaO | 0.00 |
| $Fe_2O_3$ | 0.03 |
| Cl | <0.05 |
| As | 0.00 |

The above composition demonstrated an Expansion Coefficient (0–300° C.) of $32 \times 10^{-7}$.

In addition, when the syringe 10 made of the above composition was subjected to autoclaving at elevated temperatures in excess of 120° C. at accelerating aging of 1, 3 and 5 cycles over a period of 2–3 weeks, the water for injection demonstrated a pH shift but remained within the range of 5 to 7, which can be interpreted to be maintainable over an extended period of time of at least 12 months, and preferably 24 months.

It should be appreciated that other formulations of the glass including sodium in the range of less than 8% and preferably 4% or less may be utilized. In addition, it should be appreciated that sodium is only an example of one low extractable ion glass, which is commonly referred to as a low expansion glass, other ions may be considered either alone or in combination with other ions, such as for example potassium, calcium and the like. Also, it should be appreciated that the composition may include Cerium Oxide to provide irradiation stability with respect to coloration. As such, the syringe would be sterilizable by irradiation, e.g., by gamma, electron beam, x-ray or the like, which would be advantageous over other sterilization processes where areas of difficulty to reach by the sterilization agent exist.

Use

Having described the preferred embodiment of the prefillable syringe 10 of the present invention, its use is now described. Specifically, the syringe 10 may be assembled and pre-filled by any suitable means, including those disclosed, for example, in U.S. Pat. Nos. 5,279,585 (Balkwill), 5,531,255 (Vacca), 5,519,984 (Veussink et al.), 5,373,684 (Vacca), 5,207,983 (Liebert et al.), 4,718,463 (Jurgens, Jr. et al.), and 4,628,969 (Jurgens, Jr. et al.), and PCT Application No. WO 94/13328 (Hagen), the disclosures of which are hereby incorporated by reference in their entirety.

While the preferred embodiment of present invention has been described in connection with the second type of syringe having a single chamber, it should be appreciated that it may be used in connection with other types of syringes, as well as multi-chamber syringes.

While the preferred embodiment of the present invention has been described so as to enable one skilled in the art to practice the prefillable syringe of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A syringe comprising:
    an elongate barrel having a proximal end and a distal end, with at least one chamber formed between the ends;
    a plunger sealably disposed within said barrel and movable with respect thereto;
    sealing means sealably disposed approximate said distal end of said barrel;
    at least one substance sensitive to pH shift prefilled in said chamber; and
    said barrel being made of a low extractable ion glass whereby over an extended period of time, the pH of said substance situated in said chamber of said barrel is maintained within a desired range.

2. A syringe as claimed in claim 1 wherein said substance is water for injection.

3. A syringe as claimed in claim 2 wherein said water for injection has a pH in the range of 5 to 7.

4. A syringe as claimed in claim 3 wherein the range of pH is maintained over a period of time of at least 12 months.

5. A prefillable syringe comprising:
    a generally cylindrical barrel in the shape of a hollow cylinder made of a low extractable ion glass with an open front end;
    a plunger, sealably disposed within said barrel and movable with respect thereto;
    a cylindrical stopper, having an outside diameter which is slightly larger than an inside diameter of the barrel and including means which seal the front end of the barrel; and
    a needle holder, including a collar which is attached in sealing relationship to the front end of the barrel, a neck for sealable attachment to an injection needle, the neck having a rear face which includes an aperture which functions to conduct fluid to the needle, and a hollow, internal shaft having a rear end which is sealably connected to the collar and a front end which is sealably connected to the neck; wherein the inner walls of the shaft and the rear face of the neck define one or more slots which extend from the rear end of the shaft to the aperture.

6. A prefillable syringe as claimed in claim 5 wherein a rear face of the stopper, is directed toward the plunger, a front face of the plunger is directed toward the stopper, and said faces are rotationally symmetrical and complementary.

7. A prefillable syringe as claimed in claim 5 wherein a front face of the plunger is directed toward the stopper, a rear face of the stopper is directed toward the plunger, and said faces are both flat surfaces.

8. A prefillable syringe as claimed in claim 5 further comprising a substance sensitive to pH shift disposed in said chamber.

9. A prefillable syringe as claimed in claim 5 wherein said substance is water for injection.

10. A prefillable syringe as claimed in claim 9 wherein said water for injection has a pH in the range of 5 to 7.

11. A prefillable syringe as claimed in claim 10 wherein the range of pH is maintained over a period of time of at least 12 months.

* * * * *